United States Patent
Schwendeman et al.

(12)

(10) Patent No.: US 12,377,051 B2
(45) Date of Patent: Aug. 5, 2025

(54) MICROSPHERES FOR EXTENDED, CONTROLLED RELEASE OF THERAPEUTIC AGENTS

(71) Applicant: THE REGENTS OF THE UNIVERSITY OF MICHIGAN, Ann Arbor, MI (US)

(72) Inventors: Steven P. Schwendeman, Superior Township, MI (US); Jie Tang, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 33 days.

(21) Appl. No.: 17/087,538

(22) Filed: Nov. 2, 2020

(65) Prior Publication Data

US 2021/0128484 A1    May 6, 2021

Related U.S. Application Data (60) Provisional application No. 62/929,774, filed on Nov. 2, 2019.

(51) Int. Cl.
*A61K 9/50* (2006.01)
*A61K 31/56* (2006.01)

(52) U.S. Cl.
CPC ............ *A61K 9/5031* (2013.01); *A61K 31/56* (2013.01)

(58) Field of Classification Search
CPC ............................ A61K 9/5031; A61K 31/56
See application file for complete search history.

(56) References Cited

U.S. PATENT DOCUMENTS

| | | | |
|---|---|---|---|
| 2009/0047517 A1* | 2/2009 | Caruso ................... | B05D 1/36 427/213.33 |
| 2010/0203151 A1* | 8/2010 | Hiraoka ............... | A61K 31/496 424/497 |
| 2015/0164805 A1* | 6/2015 | Schwendeman ..... | A61K 9/1652 427/2.21 |
| 2018/0085305 A1* | 3/2018 | Baillie .................. | A61K 47/10 |
| 2020/0281856 A1* | 9/2020 | Shin ..................... | A61K 31/343 |

FOREIGN PATENT DOCUMENTS

KR    20190049207    *    5/2019

OTHER PUBLICATIONS

Kang et al., Determination of diffusion coefficient of a small hydrophobic probe in poly(lactice-co-glycolide) microparticles by laser scanning confocal microscopy, Macromolecules, 36:1324-30 (2003).

Mazzara et al., Self-healing encapsulation and controlled release of vaccine antigens from PLGA microparticles delivered by microneedle patches, Bioeng. Transl. Med., 4(1):116-28 (2018).

* cited by examiner

*Primary Examiner* — Mina Haghighatian
(74) *Attorney, Agent, or Firm* — MARSHALL, GERSTEIN & BORUN LLP (57) ABSTRACT

The disclosure relates to microspheres comprising a core and a shell. More particularly the disclosure relates to microspheres for extended, controlled release of a poorly water-soluble therapeutic agent having a solubility in water of 50 μg/mL or less, the microsphere having a core comprising the therapeutic agent, and a substantially impermeable shell surrounding the core. Methods of making and using the microspheres are also provided.

14 Claims, 7 Drawing Sheets

MICROSPHERES FOR EXTENDED, CONTROLLED RELEASE OF THERAPEUTIC AGENTS

CROSS REFERENCE TO RELATED APPLICATIONS

Priority is claimed to U.S. Provisional Patent Application No. 62/929,774, filed Nov. 2, 2019, the entire disclosure of which is incorporated herein by reference.

FIELD OF THE INVENTION

The disclosure relates generally to microspheres for extended, controlled release of a therapeutic agent. More particularly, the disclosure relates to microspheres having a core and a shell, wherein the core comprises a first polymer and a therapeutic agent, and the shell comprises a second polymer. The disclosure further relates to methods of making and using the microspheres.

BACKGROUND

Injectable, biodegradable polymeric particles, such as microspheres, provide a means to deliver and control the release of molecules such as drugs, proteins, peptides and vaccine antigens. Once injected, the biodegradable polymeric particles can release the molecule over the course of hours, days or even extended periods such as weeks or months, thus eliminating the need for daily injections, and thereby improving patient acceptance and compliance. Controlled release of a drug can reduce the number of doses in an administration schedule.

An array of biodegradable polymers has been used for the microencapsulation and delivery of macromolecules. For example, copolymers of lactic acid and glycolic acid (PLGA) are biodegradable and biocompatible, and have been used in pharmaceutical products and medical devices that have been approved by the U.S. Food and Drug Administration. PLGA polymer systems are presently used in commercially available, controlled-release delivery systems for peptides including leuprolide acetate (Lupron Depot™), octreotide acetate (Sandostatin LAR™), goserelin acetate (Zoladex™ implant).

Nevertheless, significant obstacles have been encountered. Of concern is the stability of drugs during encapsulation. Methods for encapsulating drugs in biodegradable polymers can involve harsh processing conditions, including exposure to organic solvents, excess heat, and homogenization methods such as mixing, sonication, and high-speed agitation. These methods alone or in combination can destabilize drugs, such as macromolecules. Drying and micronization of a drug prior to encapsulation can further destabilize the drug.

Currently, new injectable and microneedle patch long-acting release (LAR) hormone contraceptives with extended duration (3-6 months) have gained significant attention for the purpose of improving patient compliance, the rate of continued use and reversibility of existing contraceptives. Etonogestrel (ENG) is a well-characterized third-generation progestin used in hormone contraceptives with reduced androgenic side effects and a robust safety profile. Therefore, LARs comprising ENG having and extended duration of release could fill the gap in current commercial products between the short duration (1-3 month) injectable contraceptives and longer-acting (4-12 year) contraceptive implants and intrauterine devices.

One significant obstacle of LAR contraceptives involves the desire to increase drug loading (or drug payload) in the polymer material in certain instances, particularly for transdermal microneedle-based patches where there is an unusually low upper limit on how much material can be administered (e.g., relative to standard injections). When adding more drug to the dosage form it is also problematic to maintain a steady release of drug to maintain therapeutic drug levels.

SUMMARY

Provided herein are microspheres for extended, controlled release of a therapeutic agent, comprising a core comprising a first polymer and a poorly water-soluble therapeutic agent having a solubility in water of 50 µg/mL or less, the core comprising an interconnected porous network, wherein the core has a radius of about 4 µm to about 60 µm; a substantially impermeable shell surrounding the core, thereby limiting diffusion from the core, the shell comprising a second polymer, wherein the shell has a thickness of about 1 µm to about 20 µm; wherein the first polymer and the second polymer can be the same or different, and each of the first polymer and the second polymer comprise poly(lactic acid) (PLA), poly(lactic-co-glycolic acid) (PLGA) having a high content of lactic acid, or a combination thereof.

Also provided are injectable contraceptive formulations comprising the microsphere of any one of the preceding claims and a pharmaceutically acceptable excipient.

Further provided are methods of making a microsphere for controlled release of a therapeutic agent, comprising: providing a core solution comprising a first polymer, a poorly water-soluble therapeutic agent, and a core solvent; providing a shell solution comprising a second polymer and a shell solvent; providing a coaxial needle comprising an inner section, an outer section, and a needle tip; pumping the core solution and the shell solution into the coaxial needle, wherein the core solution is pumped into the inner section and the shell solution is pumped into the outer section; applying a voltage of about 7 kV to about 12 kV to the needle tip, thereby electrospraying microspheres from the needle tip; and collecting the microspheres.

Further aspects of the disclosure may become apparent to those skilled in the art from a review of the following detailed description, taken in conjunction with the examples and appended claims. While the invention is susceptible to embodiments in various forms, described herein are specific embodiments of the invention with the understanding that the disclosure is illustrative, and is not intended to limit the invention to specific embodiments described herein.

DETAILED DESCRIPTION

The disclosure provides microspheres for extended, controlled release of therapeutic agents (i.e., drugs). As used herein, the term "microsphere" means a solid or semi-solid particle having a diameter of less than about 80 µm. Thus, particles with a major axis dimension of less than about 80 µm are suitable for use in the present invention. As used herein, the terms "therapeutic agent" and "drug" can be used interchangeably. The microspheres include a core and a shell, wherein the core includes a first polymer and a therapeutic agent and the shell includes a second polymer. The first polymer and the second polymer can be the same or different. Advantageously, the microspheres of the disclosure can sustain controlled release of a therapeutic agent for at least about 3 months and/or up to about 7 months or even longer. Additionally, the microspheres of the disclosure can demonstrate a substantially zero-order release profile.

The microspheres of the disclosure can achieve an elevated drug loading (e.g., higher than about 50%) and a continuous drug release over a specified time interval. This can be achieved by applying a core-shell design as disclosed herein that includes: (a) a core comprising mostly drug (e.g., more than 50 wt. % drug), combined with (b) a substantially impermeable shell that degrades much slower than the drug is released, thereby reducing changes to the coating and diffusion rate as drug is released. The shell includes a polymer that will eventually degrade after there is very little or no drug remaining in the core.

In embodiments, the microspheres of the disclosure can avoid an undesirable initial burst of the drug from the microsphere. In embodiments, the microspheres exhibit a substantially zero-order release profile. A substantially zero-order release profile refers to a release profile (i.e., a release rate) that is substantially constant over a period of time. As used herein, the term "substantially zero-order release profile" means that the rate of release of the therapeutic agent from the microsphere does not vary by more than about 100%, e.g., no more than about 35% (e.g., about 95%, 90%, 85%, 80%, 75%, 70%, 65%, 60%, 55%, 50%, 45%, 40%, 35%, 30%, 25%, 20%, 15%, 10%, 5% or less) over the lifetime of the microsphere. Without intending to be bound by theory, substantially zero-order release can be achieved by surrounding a core comprising a drug with a shell comprising a polymer that is permeable to both drug and water. When the core becomes hydrated under physiological conditions, the drug will dissolve until it reaches its saturation concentration (i.e., solubility). For poorly water-soluble drugs, this saturation concentration is very low. Thus, the core serves as a saturated reservoir of the drug. Release of the drug occurs when the drug permeates into the shell from the reservoir (i.e., core) and then diffuses across the shell into the body. The diffusion is believed to be a multi-step diffusion including hydration/saturation of the core, diffusion through the shell, as well as the slow degradation of the polymer in the shell and/or core.

Thus, the microspheres of the disclosure can provide a drug delivery system in which drug release from the core is advantageously controlled, by providing a shell material having a permeability that does not change significantly change over time, such that shell serves to consistently control and indeed limit the rate of drug delivery from the core over the course of drug delivery. Thus, the shell typically degrades at a rate that is much slower than the release rate of the drug from the microsphere. The most commonly used drug microparticle formulation techniques often result in release profiles that are identified by a quick, "initial burst" release of the therapeutic agent from the particle. However, the present inventors have successfully developed a therapeutic agent delivery system (i.e., microspheres) that can advantageously provide a desired release time frame with a decreased initial burst release and particle size distribution, as well as an increased therapeutic agent loading for an injectable microsphere formulation. Without intending to be bound by theory, in embodiments, the microspheres of the disclosure can demonstrate a substantially zero-order release profile by selecting and controlling the amount of each of the first polymer, the second polymer, and the therapeutic agent, as well as the sizes and thicknesses of the core, the shell, and/or the microsphere as a whole as described herein.

Furthermore, and without intending to be bound by theory, it is believed that if the core, including the first polymer and the drug, was immersed in water without a surrounding shell, substantially all of the drug would be released very quickly, because the loading of drug would be well above the percolation threshold, and all of the drug in the polymer matrix would have access to pores that percolate to the surface of the polymer.

Microsphere Composition

As provided herein, the microspheres of the disclosure include a core and a shell. The core includes a first polymer and a poorly water-soluble therapeutic agent having a water-solubility of less than about 50 µg/mL. The shell includes a second polymer. The first polymer and the second polymer can be the same or different. Each of the first and the second polymer can include poly(lactic acid), poly(lactic-co-glycolic acid) having a high lactic acid content, or a mixture thereof. In embodiments, the first and the second polymer are the same. In embodiments, the first polymer and the second polymer are different.

Core Composition

The core includes a first polymer. As described above, the first polymer can be the same or different than the second polymer. The first polymer can include PLA, PLGA having a high lactic acid content, or a combination thereof. Without intending to be bound by theory, it is believed that a PLGA having a high lactic acid content will degrade more slowly than a PLGA having a 1:1 glycolic acid to lactic acid ratio or less. Accordingly, in embodiments, the content of lactic acid in the PLGA can be at least about 60%, 70%, 75%, or 80%, and/or up to about 75%, 80%, 90% or 95%, such as about 60% to about 95%, about 70% to about 90%, or about 75% to about 80%, based on the total content of glycolic acid and lactic acid monomer units in the PLGA. In embodiments, the first polymer comprises PLA. In embodiments, the first polymer comprises PLGA having a high lactic acid content. In embodiments, the first polymer is provided by a combination of PLA and PLGA having a high lactic acid content.

The first polymer can have an inherent viscosity ranging from about 0.1 dL/g to about 2.0 dL/g, for example at least about 0.1, 0.2, 0.3, 0.4, 0.5, 0.6, 0.75, 0.9 or 1.0 and/or up to about 1.0, 1.2, 1.4, 1.6, 1.8 or 2.0 dL/g. In embodiments, the first polymer has an inherent viscosity of about 0.1 dL/g to about 2.0 dL/g, about 0.3 dL/g to about 1.7 dL/g, about 0.5 dL/g to about 1.5 dL/g, about 0.75 dL/g to about 1.25 dL/g, or about 0.8 dL/g to about 1.0 dL/g. The first polymer can have a weight average molecular weight ranging from at least about 50, 55, 60, 65, 70, or 75 kDa and/or up to about 70, 75, 80, 85, 90, 95, or 100 kDa. In embodiments, the first polymer has a weight average molecular weight ranging from about 50 kDa to about 100 kDa, about 60 kDa to about 90 kDa, about 70 kDa to about 80 kDa, or about 75 kDa to about 100 kDa.

The first polymer can be present in the core in an amount of at least about 10, 15, 20, 25, 30, or 35 wt %, and/or up to about 25, 30, 35, 40, 45, 50, or 65 wt %, based on the total weight of the core. In embodiments, the first polymer is present in the core in an amount of about 10 wt % to about 65 wt %, for example, between about 15 wt. % and 40 wt. %, about 20 wt % to about 50 wt %, about 25 wt % to about 50 wt %, or about 30 wt % to about 40 wt %, based on the total weight of the core.

The core further includes a poorly water-soluble therapeutic agent. As used herein, the term "poorly water-soluble" means that the therapeutic agent has a water solubility of about 50 µg/mL or less, about 40 µg/mL or less, about 30 µg/mL or less, about 20 µg/mL or less, about 15 µg/mL or less, about 10 µg/mL or less, or about 5 µg/mL or less, for example about 50, 45, 40, 35, 30, 25, 20, 15, 10, 5, 4, 3, 2, 1, 0.5, 0.1, or 0.01 µg/mL or less. The particular therapeutic agent is not particularly limited (i.e., so long as it is poorly water-soluble), and can include contraceptives, anticancer agents, antibiotics, antivirals, and the like. An example of a suitable anticancer agents includes, but is not limited to, paclitaxel. In embodiments, the therapeutic agent comprises a poorly water-soluble steroid. In embodiments, the therapeutic agent comprises a poorly water-soluble contraceptive steroid such as a poorly water-soluble androgen (or anabolic steroid), a poorly water-soluble estrogen, or a poorly water-soluble progestogen. Examples of suitable poorly water-soluble steroids include, but are not limited to, oxandrolone, testosterone, nandrolone, estradiol, diethylstrilbestrol, etonogestrel, norethindrone, progesterone, nesterone, derivatives thereof, and combinations thereof. In embodiments, the poorly water-soluble therapeutic agent comprises etonogestrel (ENG). A microsphere can include a single therapeutic, or a combination of two or more therapeutic agents.

The therapeutic agent can be included in the core in an amount of at least about 35, 40, 45, 50, 60, 65, or 70 wt % and/or up to about 65, 70, 75, 80, 85 or 90 wt %, based on the total weight of the core. In embodiments, the therapeutic agent is present in the core in an amount of about 35 wt % to about 90 wt %, for example, between about 60 wt. % and 85 wt. %, about 40 wt % to about 75 wt %, about 50 wt % to about 65 wt %, or about 60 wt % to about 80 wt %, based on the total weight of the core.

Advantageously, the microspheres of the disclosure are capable of high therapeutic agent loading, for example up to a drug loading of at least about 80%, at least about 75%, at least about 70%, at least about 60%, at least about 59%, at least about 58%, at least about 57%, at least about 56%, at least about 55%, at least about 54%, at least about 53%, at least about 52%, at least about 51%, at least about 50%, at least about 49%, at least about 45%, at least about 40%, or at least about 30%. Drug loading can be determined by dividing the mass of the therapeutic agent in the microsphere by the total mass of the microsphere (i.e., the total mass of the core and the shell) and multiplying by 100%.

Similarly, the microspheres of the disclosure can provide excellent drug loading (i.e., encapsulation) efficiency, for example at least about 95%, 90%, 92%, 95%, 98%, or 99% and/or up to about 95%, 98%, 99%, 99.5%, 99.9% or 100% efficiency. Drug loading efficiency can be calculated by dividing the mass of the therapeutic agent in the microsphere by the initial mass of the therapeutic agent in the core (i.e., loading) solution, and multiplying by 100%.

In embodiments, the weight ratio of the first polymer to the therapeutic agent in the core can range from about 1:1 to about 1:4, for example about 1:1, 1:1.5, 1:2, 1:2.5, 1:3, 1:3.5 or 1:4. In embodiments, the weight ratio of the first polymer to the therapeutic agent in the core is about 1:1 to about 1:3.5, about 1:2 to about 1:4, about 1:2 to about 1:3, or about 1:2.5 to about 1:3.5.

The core can have a radius, and similarly the cores of a plurality of microspheres can be described as having an average radius, of about 4 μm to about 60 μm, for example at least about 4, 5, 7, 10, 15, 20, 25, 30, or 35 μm and/or up to about 30, 35, 40, 45, 50, 55 or 60 μm. In embodiments, the core has a radius, and a plurality of particles can have an average radius, of about 4 μm to about 50 μm, about 5 μm to about 45 μm, about 10 μm to about 40 μm, about 15 μm to about 25 μm, or about 20 μm to about 30 μm. Core radius can be measured by confocal microscopy when the core contains a fluorescently labeled dye.

In embodiments, the core comprises auxiliary components, such as, a solubilizer. The solubilizer can be included to adjust the solubility of the therapeutic agent within the core. Examples of suitable solubilizers can include cocrystals and/or coformers, such as triethyl citrate and saccharin.

In embodiments, the core consists of the therapeutic agent and the first polymer.

The interactions between the first polymer, the therapeutic agent, and any other additional ingredients included therein provide for an interconnected porous network. That is, the therapeutic agent in the core can interconnect and move relatively freely among the first polymer. Therefore, in order to minimize an initial burst of the therapeutic agent from the porous network of the core and into the surrounding environment (i.e., a physiological environment), the core is surrounded by a shell. Without intending to be bound by theory, the interconnected porous network of the core can be formed, in part, due to the fact that the core has a greater amount of the therapeutic agent relative to the amount of first polymer. As the therapeutic agent is not significantly soluble in the first polymer, most of the therapeutic agent is dispersed within the core as opposed to being dissolved in the first polymer, thereby creating a network of pores in the core.

Shell Composition

The shell of the microsphere is substantially impermeable. Without intending to be bound by theory, the shell creates a diffusion barrier so that the drug concentration at the inside surface of the shell is substantially equal to the solubility of the drug. Because the water-solubility of the drug is so low such that negligible osmotic pressure is generated and the shell polymer has not significantly eroded, the shell will remain substantially intact until there is almost no drug remaining in the core. Accordingly, the driving force for diffusion (i.e., the diffusion coefficient) can be related, in part, to the water-solubility of the drug and the polymer/drug partition coefficient of the drug. Without intending to be bound by theory, presuming no change in the drug solid state in the core or limited drug instability, if the diffusion coefficient and partition coefficient do not change over the lifetime of the microsphere, then the driving force and the resistance to diffusion will not change and a substantially zero order release of the therapeutic agent will be observed. The diffusion coefficient for the shell that can allow for the substantially zero-order release described herein can generally be about $10^{-11}$ cm$^2$/s to about $10^{-14}$ cm$^2$/s. Diffusion coefficients within this range can provide a substantially impermeable shell as described herein.

Furthermore, in contrast with the core, the shell can be substantially free of an interconnected porous network. As used herein, "substantially free of an interconnected porous network" means that, while the shell can have a porosity of about 50% at most, the pores of the shell are not interconnected so as to allow the therapeutic agent to freely move throughout (and through) the shell. Polymer healing during incubation also may help to maintain this barrier should small holes or cracks appear. Rather, the pores of the shell are isolated, thereby inhibiting the diffusion of the therapeutic agent out of the core of the microsphere. Accordingly, the total porosity of the shell (i.e., the amount of isolated pores) is no greater than about 50%, preferably no greater than about 40%, more preferably no greater than about 30%, and most preferably no greater than about 20%.

The shell includes a second polymer. The second polymer can generally be as described for the first polymer in the core. The second polymer can be the same or different than the first polymer. The second polymer can include PLA, PLGA having a high lactic acid content, or a combination thereof. In embodiments, the second polymer includes PLA. In embodiments, the second polymer includes PLGA having a high lactic acid content. In embodiments, the second polymer includes a combination of PLA and PLGA having a high lactic acid content.

The second polymer can have an inherent viscosity ranging from about 0.1 dL/g to about 2.0 dL/g, for example at least about 0.1, 0.2, 0.3, 0.4, 0.5, 0.6, 0.75, 0.9 or 1.0 and/or up to about 1.0, 1.2, 1.4, 1.6, 1.8 or 2.0 dL/g. In embodiments, the second polymer has an inherent viscosity of about 0.1 dL/g to about 2.0 dL/g, about 0.3 dL/g to about 1.7 dL/g, about 0.5 dL/g to about 1.5 dL/g, about 0.75 dL/g to about 1.25 dL/g, or about 0.8 dL/g to about 1.0 dL/g. The second polymer can have a weight average molecular weight ranging from at least about 50, 55, 60, 65, 70, or 75 kDa and/or up to about 70, 75, 80, 85, 90, 95, or 100 kDa. In embodiments, the first polymer has a weight average molecular weight ranging from about 50 kDa to about 100 kDa, about 60 kDa to about 90 kDa, about 70 kDa to about 80 kDa, or about 75 kDa to about 100 kDa.

In embodiments, the second polymer will not substantially degrade for at least about 3, 4, 5, 6, or 7 months when exposed to physiological conditions. In embodiments, the second polymer will not substantially degrade for at least about 3, 4, 5, 6, or 7 months when exposed to physiological conditions. As used herein, the term "substantially degrade" refers to the point at which the polymer has degraded via hydrolysis to lower than a weight average molecular weight of roughly 25 kDa, i.e., a point where the molecular diffusion of the therapeutic agent would substantially increase as the molecular weight of the polymer drops further.

The shell can consist essentially of the second polymer. As used herein, the term "consist essentially of" means that the second polymer can be present in the shell in an amount of at least about 90, 92, 95, 97, 98, 99, 99.5, 99.9 or 100 wt %, based on the total weight of the shell. Residual components may be present in minor amounts, such as those used in preparing the shell solution prior to formation of the microsphere.

The shell can be substantially free of the therapeutic agent, prior to the microsphere being exposed to an aqueous solution (e.g., physiological conditions upon administration to a patient). As used herein, "substantially free of the therapeutic agent" means that the shell suitably contains less than about 5, 4, 3, 2, 1, 0.5, 0.1, or 0.01 wt % of the therapeutic agent, prior to being exposed to an aqueous solution.

In embodiments, the shell comprises more than 90% of the second polymer, for example, the shell consists of the second polymer.

In embodiments, the shell can further include a small molecule. A small molecule can be included in the shell in order to compete with release of the drug in the core, thereby advantageously decreasing the initial burst release of the drug from the microsphere caused by the migration of drug from core to shell. Any small molecule that has similar physical and chemical properties to the drug(s) in the core and are safe in humans can be used. For example, any small molecule that has similar solubility, partition coefficient efficiency, pKa, etc. to the drug(s) in the core can be used. In embodiments, the small molecule is hydrophobic. Examples of suitable small molecules include, but are not limited to, cholesterol, lipophilic vitamins, or combinations thereof. Derivatives of the small molecules can also be used, such as metabolites of cholesterol or of lipophilic vitamins. Metabolites of cholesterol include, for example, cholesteryl esters and steroid hormones. Examples of suitable vitamins include vitamin E and vitamin D3, and any derivatives thereof. In embodiments, the shell includes cholesterol. When present, the small molecule can be present in an amount of about 0.1 wt % to about 30 wt %, based on the total weight of the shell, for example at least about 0.1, 0.2, 0.5, 1, 2, 3, 4, 5, 10, 15, or 20 wt % and/or up to about 7, 8, 9, 10, 15, 20, 25, 27, or 30 wt %, based on the total weight of the shell. In embodiments, the small molecule is present in an amount of about 0.5 wt % to about 30 wt %, about 1 wt % to about 15 wt %, about 5 wt % to about 25 wt %, about 10 wt % to about 20 wt %, about 2 wt % to about 6 wt %, or about 3 wt % to about 5 wt %. In embodiments, the small molecule is present in an amount of about 1 wt % to about 40 wt %, based on the total weight of the drug in the core, for example at least about 1, 5, 10, 15, 20, or 25 wt % and/or up to about 10, 15, 20, 25, 30, 35, or 40 wt %, based on the total weight of the drug in the core. The small molecule can be present in an amount of about 1 wt % to about 40 wt %, about 5 wt % to about 35 wt %, about 5 wt % to about 30 wt %, about 1 wt % to about 20 wt %, about 10 wt % to about 40 wt %, or about 15 wt % to about 30 wt %, based on the total weight of the drug in the core.

Without intending to be bound by theory, incorporation of small molecules (e.g., hydrophobic small molecules) in the shell composition may decrease the partitioning of drug into the shell layer during formation of the microsphere and during release. Reduced partitioning of the drug into the shell layer can reduce the rate of drug release. Additionally, the presence of a small molecule (e.g., a hydrophobic small molecule) may also impede water uptake in the shell to decrease the effective diffusion coefficient of the drug in the shell polymer.

In embodiments, the shell can further include a plasticizer. As used herein, the term "plasticizer" refers to a material that can be added to adjust the diffusion coefficient of the shell. Without intending to be bound by theory, the plasticizer should be particularly selected and added in an amount that does not disrupt the ability of the shell to provide a substantially impermeable barrier to the therapeutic agent in the core.

The shell can have a thickness, and similarly the shells of a plurality of microspheres can be described as having an average thickness, of about 1 μm to about 20 μm, for example at least about 1, 2, 3, 4, 5, 7, 10, or 12 and/or up to about 10, 12, 15, 17, 19, or 20 μm. Shell thickness can be measured by confocal microscopy when the shell contains a fluorescently labeled dye. In embodiments, the shell has a thickness, and the shells of a plurality of microspheres can have an average thickness, of about 1 μm to about 19 μm, about 2 μm to about 18 μm, about 5 μm to about 15 μm, about 7 μm to about 12 μm, or about 10 μm to about 20 μm. In embodiments, the shell has a thickness, and the shells of a plurality of microspheres can have an average thickness, of about 2 μm to about 15 μm.

The microsphere of the disclosure can have a particle size (i.e., diameter), and a plurality of microspheres can have an average particle size, ranging from about 5 μm to about 80 μm, for example at least about 5, 10, 15, 20, 25, 30, 35, 40, or 45 μm and/or up to about 30, 35, 40, 45, 50, 55, 60, 65, 70, 75 or 80 μm. In embodiments, the microsphere can have a particle size, and a plurality of microspheres can have an average particle size, of about 5 μm to about 75 μm, about 10 μm to about 70 μm, about 12 μm to about 65 μm, about 15 μm to about 60 μm, about 20 μm to about 55 μm, or about 30 μm to about 50 μm. The particle size can represent a weight-, number-, surface area-, or volume-average size for a particle size distribution of the microspheres. Particle sizes can be quantified by SEM images, and quantified using a Master Sizer 2000 laser diffraction particle size analyzer (Master Sizer 2000, Malvern Instruments Ltd. Malvern, UK)

Uses of the Microspheres

The microspheres of the disclosure can be used in injectable compositions. For example, the disclosure provides injectable contraceptive formulations including the microspheres of the disclosure. The formulations can further include a pharmaceutically acceptable excipient.

Advantageously, the microspheres of the disclosure can provide an injectable contraceptive that has a controlled release of the drug which can be adjusted to stop at, or after, a predetermined period of time such that the patient can be fertile again, if desired.

The pharmaceutically excipient can include sterile water, saline, or a buffered solution. Additional excipients can include, but are not limited to carboxymethylcellulose sodium, D-mannitol, polysorbate, and combinations thereof, which can be added to help resuspension of microspheres.

The microspheres can advantageously be injected to a subject via incorporation into a microneedle.

Methods of Making the Microspheres

Also provided herein are methods of making the microspheres of the disclosure using electrohydrodynamic (EHD) jetting. Advantageously, EHD jetting has been shown to be very efficient in controlling the microsphere size, morphology and monodispersity.

The methods of the disclosure include providing a core solution comprising a first polymer, a poorly water-soluble therapeutic agent, and a core solvent; providing a shell solution comprising a second polymer and a shell solvent; providing a coaxial needle comprising an inner section, an outer section, and a needle tip; pumping the core solution and the shell solution into the coaxial needle, wherein the core solution is pumped into the inner section and the shell solution is pumped into the outer section; applying a voltage of about 7 kV to about 12 kV to the needle tip, thereby electrospraying microspheres from the needle tip; and collecting the microspheres.

Core Solution

As provided herein, the core solution includes a first polymer, a poorly water-soluble therapeutic agent, and a core solvent. The first polymer and the poorly water-soluble therapeutic agent are described in detail above.

The core solvent can include an organic solvent. For example, in embodiments, the core solvent includes chloroform, ethyl acetate, xylene, dichloromethane, or a mixture thereof. In embodiments, the core solvent includes chloroform. In embodiments, the core solvent includes ethyl acetate. In embodiments, the core solvent includes xylene. In embodiments, the core solvent includes dichloromethane. In embodiments, the core solvent includes two or more of chloroform, ethyl acetate, dichloromethane and xylene. In embodiments, the core solvent includes chloroform and ethyl acetate. In embodiments, the core solvent includes dichloromethane and ethyl acetate. In embodiments, the core solvent consists of chloroform. When the core solvent includes two solvents, the ratio of the solvents can range from about 1:3 to about 3:1, about 1:2 to about 2:1, or about 1:1.5 to about 1.5:1, for example, about 1:3, 1:2.5, 1:2, 1:1.5, 1:1, 1.5:1, 2:1, 2.5:1, or 3:1. In embodiments, the poorly water-soluble therapeutic agent is readily soluble in the core solvent. In embodiments, the poorly water-soluble therapeutic agent is poorly soluble in the core solvent. In embodiments wherein the poorly water-soluble therapeutic agent is also poorly soluble in the core solvent, the therapeutic agent can be suspended within the core solvent (i.e., thereby forming a core suspension, which can be just as suitable for use in preparing the microspheres of the disclosure as the core solution wherein the therapeutic agent is dissolved in the core solvent).

The core solution can include the first polymer in an amount of about 5% w/v to about 30% w/v, for example at least about 5, 10, 15, or 20% w/v and/or up to about 15, 20, 25, or 30% w/v. In embodiments, the core solution comprises about 5% w/v to about 25% w/v, about 10% w/v to about 20% w/v, or about 25% w/v or about 20% w/v of the first polymer. In embodiments, the core solution comprises about 5% w/v to about 20% w/v of the first polymer.

The core solution can include the poorly water-soluble therapeutic agent in an amount of about 10% w/v to about 60% w/v, for example at least about 10, 15, 20, 25, 30, 35, or 40% w/v and/or up to about 30, 35, 40, 45, 50, 55, or 60% w/v. In embodiments, the core solution comprises about 10% w/v to about 55% w/v, about 15% w/v to about 45% w/v, about 20% w/v to about 40% w/v, or about 25% w/v to about 35% w/v. In embodiments, the core solution comprises about 10% w/v to about 40% w/v of the poorly water-soluble therapeutic agent.

The weight ratio of the first polymer to the therapeutic agent in the core solution can range from about 1:1 to about 1:4, for example about 1:1, 1:1.5, 1:2, 1:2.5, 1:3, 1:3.5, or 1:4.

Shell Solution

As provided herein, the shell solution includes a second polymer and a shell solvent. The second polymer is described in detail above. In general, the substantial impermeability of the shell can be formed during preparation of the microsphere, when the shell solvent evaporates. Faster solvent evaporation from the shell of microspheres can form a polymer-rich phase in the shell that is less porous and more dense. Therefore, increasing the amount of the second polymer in the shell solution, using higher molecular weight polymers in the shell solution, incorporating additional small molecules that increase density of the shell solution, using shell solvents with lower boiling points, and using polymers with increased polymer strength can each increase the impermeability of the shell and reduce the initial burst release of the drug from the microsphere upon being introduced to an aqueous or physiological environment. After the initial burst phase, the free volume of the second polymer in the shell and presence of small molecules in the shell can control the permeability of the shell.

The shell solvent can include an organic solvent. For example, in embodiments, the shell solvent includes chloroform, ethyl acetate, xylene, dichloromethane, or a mixture thereof. In embodiments, the shell solvent includes chloroform. In embodiments, the shell solvent includes ethyl acetate. In embodiments, the shell solvent includes xylene. In embodiments, the shell solvent includes dichloromethane. In embodiments, the shell solvent includes two or more of chloroform, xylene, dichloromethane and ethyl acetate. In embodiments, the shell solvent includes chloroform and ethyl acetate. In embodiments, the shell solvent includes dichloromethane and ethyl acetate. When the core solvent includes two solvents, the ratio of the solvents can range from about 1:3 to about 3:1, about 1:2 to about 2:1, or about 1:1.5 to about 1.5:1, for example, about 1:3, 1:2.5, 1:2, 1:1.5, 1:1, 1.5:1, 2:1, 2.5:1, or 3:1. In embodiments, the shell solvent comprises a 1:1 mixture of chloroform and ethyl acetate. In embodiments, the shell solvent comprises a 1:1 mixture of dichloromethane and ethyl acetate.

Without intending to be bound by theory, it may be advantageous to include a shell solvent and/or a core solvent with lower boiling points (e.g., dichloromethane (39° C.) and/or chloroform (61° C.)). In particular, it is believed that including a solvent with a lower boiling point can result in less partitioning of the drug from the core into the shell, as the microsphere can dry faster during the manufacturing process. In embodiments, when two or more shell solvents are used, the shell solution can have an average boiling point of about 40° C. to about 70° C., for example about 45° C. to about 65° C., about 50° C. to about 70° C., or about 55° C. to about 70° C., such as 45, 50, 55, 56, 57, 58, 59, 60, 65, 66, 67, 68, 69, or 70° C. The average boiling point can be the weighted average of the solvents in the shell solution. For example, the average boiling point of a shell solution comprising a 1:1 mixture of dichloromethane and ethyl acetate is 58° C. (i.e., (0.5×39° C.)+(0.5×77° C.)).

The shell solution can include the second polymer in an amount of about 5% w/v to about 80% w/v, for example at least about 5, 10, 15, 20, 25, 30, 35, 40, 45, or 50% w/v and/or up to about 35, 40, 45, 50, 55, 60, 65, 70, 75, or 80% w/v. In embodiments, the shell solution comprises about 5% w/v to about 20% w/v of the second polymer.

As described above, the shell can include a small molecule, such as cholesterol. The shell solution can include the small molecule in an amount of about 0.1% w/v to about 10% w/v, based on the total weight of the shell solution, for example at least about 0.1, 0.2, 0.5, 1, 2, 3, 4, 5, 6, 7% w/v and/or up to about 3, 4, 5, 6, 7, 8, 9, or 10% w/v, based on the total weight of the shell solution. In embodiments, the small molecule is present in an amount of about 0.5% w/v to about 10% w/v, about 1% w/v to about 7% w/v, about 2% w/v to about 6% w/v, or about 3% w/v to about 5% w/v.

In embodiments, the shell solution is free of the therapeutic agent. As used herein, "free of the therapeutic agent" means that prior to making the microspheres, the shell solution contains no intentionally added therapeutic agent.

The weight ratio of the first polymer to the therapeutic agent in the core solution can range from about 1:1 to about 1:4, for example about 1:1, 1:1.5, 1:2, 1:2.5, 1:3, 1:3.5, or 1:4. In embodiments, the weight ratio of the first polymer to the therapeutic agent in the core solution is about 1:1 to about 1:3.5, about 1:2 to about 1:4, about 1:2 to about 1:3, or about 1:2.5 to about 1:3.5.

Coaxial Needle and Use to Make Microspheres

The method includes providing a coaxial needle comprising an inner section, an outer section, and a needle tip. The inner section and the outer section of the needle are defined and separated by an impermeable barrier. An example of a coaxial needle can be seen in FIG. 1. The inner section can have a gauge of about 15. The outer section can have a gauge of about 25.

The method includes pumping the core solution and the shell solution into the coaxial needle, wherein the core solution is pumped into the inner section and the shell solution is pumped into the outer section. The pumping rate (i.e., the pump speed), of each of the core solution and the shell solution can impact the formation of the microspheres, as opposed to polymer fibers. In embodiments, the core solution is pumped at a rate of about 0.3 mL/hr to about 0.5 mL/hr, for example about 0.3, 0.35, 0.4, 0.45, or 0.5 mL/hr. In embodiments, the shell solution is pumped at a rate of about 0.3 mL/hr to about 0.5 mL/hr, for example about 0.3, 0.35, 0.4, 0.45, or 0.5 mL/hr.

The method further includes applying a voltage of about 7 kV to about 12 kV to the needle tip, thereby electrospraying microspheres from the needle tip. The voltage can be provided by any suitable power generator. The voltage applied can range from about 7 kV to about 12 kV, for example about 7, 7.5, 8, 8.5, 9, 9.5, 10, 10.5, 11, 11.5, or 12 kV. Upon applying a voltage, a Taylor-Cone at the needle tip forms (FIG. 1), and allows individual microspheres according to the invention to form and electrospray from the coaxial needle.

The method includes collecting the microspheres (from the electrospray), on a grounded collector. By "grounded" collector, it is meant that once the microspheres contact the collector, any remaining charge thereon can be removed from the microsphere. In embodiments, the microspheres are collected on a teflon/aluminum foil. In embodiments, the microspheres are collected in a water bath. The water bath can include a surfactant, such as polyvinyl alcohol. In embodiments, the water bath includes 1% polyvinyl alcohol (PVA).

The working distance between the coaxial needle (i.e., the jetting needle) and the grounded collector can be in a range of about 3 cm to about 30 cm, about 5 cm to about 20 cm, or about 10 cm to about 15 cm, for example at least about 3, 4, 5, 6, 7, 8, 9, 10, 11, 12, 13, 14, 15, 16, 17, 18, 19 or 20 and/or up to about 12, 13, 14, 15, 16, 17, 18, 19, 20, 21, 22, 23, 24, 25, 26, 27, 28, 29, or 30 cm. Without intending to be bound by theory, the working distance can impact the particle size of the microspheres, as well as the apparent dryness of the shell of the microspheres. In general, as the working distance increases, the applied voltage should be proportionately increased, in order for the electrospray to reach the collector.

EXAMPLES

The following examples evaluated the ability to encapsulate ENG into a high-drug loading core-shell structured PLA microsphere (ENG-MS) by employing an elecrtrohydrodynamic (EHD) co-jetting method to achieve a diffusion-controlled 3-6 month continuous therapeutic agent release.

Methods and Materials

Figure 1:
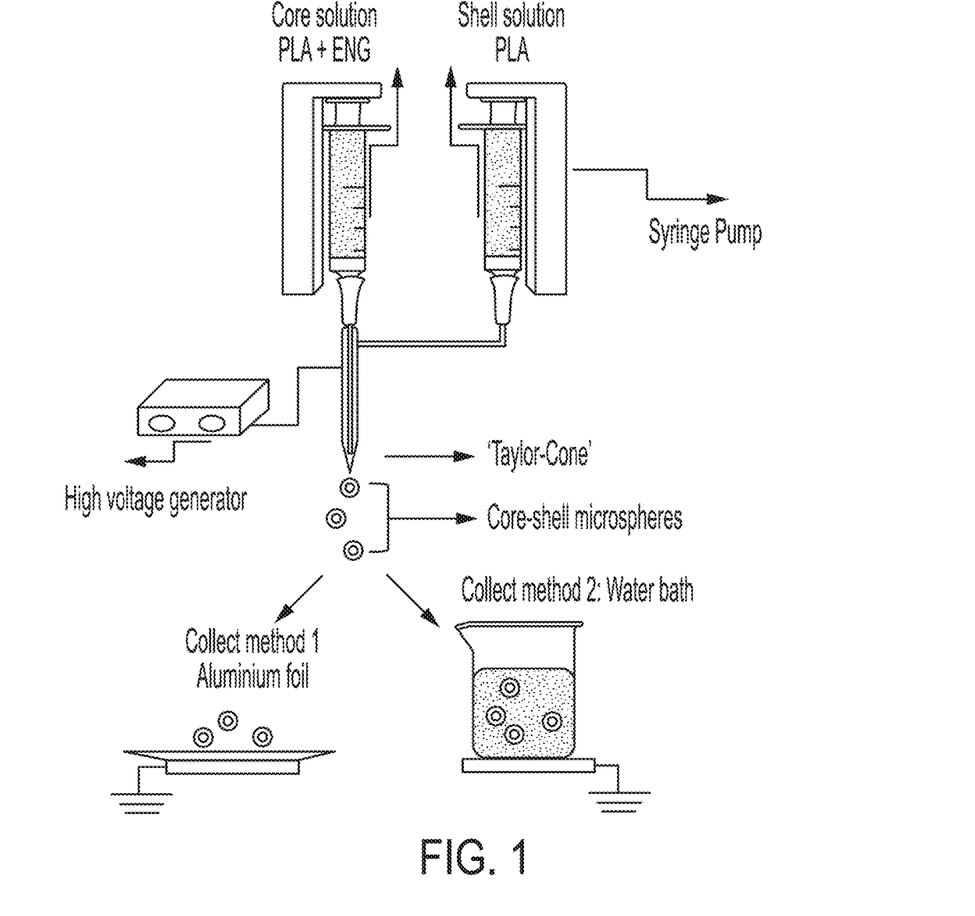
FIG. 1 is an illustration of a method of preparing a core-shell structured microsphere according to the disclosure.

Microspheres were prepared using an EHD co-jetting method, as generally shown in FIG. 1. Specifically, to prepare the therapeutic agent encapsulated core-shell structured microspheres, the outer (15 gauge) and inner (25 gauge) sections of a coaxial needle were filled with a shell polymer solution and core polymer/drug solution, respectively, and connected with two syringe pumps to control the flow rate of jetting of core and shell solution. A high voltage was applied to the needle tip via a power generator to form a stable Taylor-Cone jet at the needle tip, and the electrosprayed particles were accelerated towards the grounded collector. Particles were collected at certain working distance below the needle exit by either (A) a Teflon/aluminum foil (Method 1), or (B) a water bath with 1% polyvinyl alcohol (PVA, 88% hydrolyzed, MW 25,000) (Method 2).

Confocal Microscopy was used to image the resulting microspheres for core-shell structure validation. A green fluorescent dye—PTDPV-Poly[tris(2,5-bis(hexyloxy)-1,4-phenylenevinylene)-alt-(1,3-phenylenevinylene), and blue dye—MEHPV, Poly[2-methoxy-5-(2-ethylhexyloxy)-1,4-phenylenevinylene] was added into polymer solution during formulation preparation to label shell and core, respectively. Labeled microspheres were injected on to the glass slide sitting on the grounded collector, and imaged via confocal laser scanning microscopy (CLSM)(Nikon A1, Tokyo, Japan).

A TESCAN Scanning Electron Microscope (SEM) was used for microsphere morphology evaluation. The surface morphology of microspheres was examined via a Tescan MIRA3 FEG electron microscope (SEM) (TESCAN Brno, s.r.o., Kohoutovice, Czech Republic). Microspheres were mounted onto a brass stub using double-sided adhesive tape, and sputter-coated with gold for 60 s at 40 W under vacuum. Images were taken at an excitation voltage of 5 kV.

The in vitro release method for microspheres was evaluated via dialysis with nylon mesh bags having a pore size of 1 micron. The medium in which the release was evaluated with a PBS+0.02% polysorbate 80 (Tween 80) solution having a pH of 7.4 (PBST release medium).

Pharmacokinetic data were obtained for Sprague Dawley (SD) female rats, and a quantification method on High performance Liquid Chromatography Coupled with Quadrupole Time of Flight Mass Spectrometry (HPLC/Q-TOF MS) was developed to monitor the amount of ENG in rat serum. Briefly, an eight-point calibration curve was made by spiking 100 μL of rat serum with 10 μL ENG working solution corresponding to final concentration of 50, 100, 250, 500, 1000, 2500, 5000 and 10000 μg/mL respectively, and 10 μL of internal standard (200 ng/ml ENG-d7 in 50% ACN/$H_2O$). The mixtures were vortexed for 20 s, then passed through the Oasis HLB cartridge (1 $cm^3$, 30 mg) for solid phase extraction. The cartridge was first pre-conditioned with 1 mL ACN, and 1 mL water, then washed with 1 mL water and 1 mL 10% ACN after serum samples were loaded. Finally, ENG and internal standard were eluted with 1 mL ACN, and evaporated under nitrogen stream to dryness. The residue was reconstituted with 80 μL 50% ACN and 20 μL hydroxylamine hydrochloride solution (1M), incubated at 60° C. for 25 min for completed derivatization of drug. After centrifuge, 70 μL upper layer was transferred into UPLC vials for further analysis. Derivatized ENG and ENG-d7 were separated on an Agilent C18 column (100 mm×3.0 mm i.d., 2.7 μm particle size) at 40° C. and a gradient elution of solvent A (acetonitrile containing 0.1% formic acid) and solvent B (water containing 0.1% formic acid) at flow rate of 0.5 mL/min as follows: 0-0.5 min (30% A), 0.5-1 min(30-60% A), 1-3 min (60% A), 3-3.5 min (60-90% A), 3.5-4.5 min (90% A), followed by recovery with initial conditions for 2 min. The injection volume was 15 μL. The mass spectra of derivatized ENG and ENG-d7 were acquired with electrospray ionization (ESI) source in the positive ion mode condition. Full scan mode was used. Extraction of derivatized ENG and ENG-d7 spectra peaks at 340.22 and 347.27 with a width of 0.02 Da was used to pick up the extracted ion chromatograms (EICs) from Total ion chromatogram (TIC) for quantification.

Example 1—Preparation and Morphological Evaluation of Microspheres

Four microsphere formulations having different amounts of PLA and ENG were prepared in order to evaluate the effect of the formulation of microsphere morphology. Each formulation was prepared to target a theoretical drug loading of 50%. The formulations are provided in Table 1, below. The PLA used within the core solution was Resomer® R 205 S PLA (EVONIK®, having an inherent viscosity of 0.55-0.75 dL/g) in chloroform. The ENG was also provided in chloroform. The PLA used within the shell solution was Resomer® R 205 S PLA in a 1:1 w/v chloroform/ethyl acetate solution. The jetting conditions for the preparation of the microspheres were kept constant for each of formulations 1-4.

TABLE 1

Microsphere Formulations

| | Core | | Shell | Theoretical | Jetting Conditions | | |
| | | | | | Core pump | Shell pump | |
| Formulation | PLA % (w/v) | ENG % (w/v) | PLA % (w/v) | Drug Loading (%) | speed (mL/hr) | speed (ml/hr) | Voltage |
|---|---|---|---|---|---|---|---|
| 1 | 10 | 20 | 10 | 50 | 0.4 | 0.4 | 7→12 |
| 2 | 12 | 24 | 12 | 50 | | | |
| 3 | 15 | 30 | 15 | 50 | | | |
| 4 | 18 | 30* | 18 | 45.5 | | | |

*36% (w/v) ENG cannot be dissolved in 18% (w/v) PLA-chloroform solution

Figure 2A:
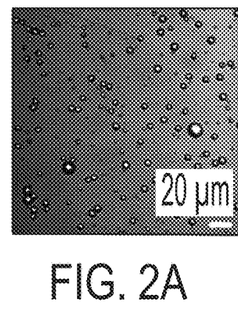
FIG. 2A is a microscopic image of microspheres prepared according to the disclosure, with 10% w/v PLA and 20% w/v ENG in the core solution, and 10% w/v PLA in the shell solution.
Figure 2B:
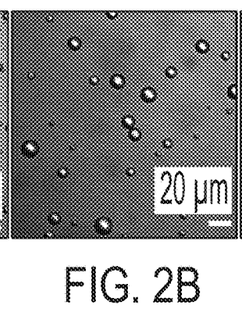
FIG. 2B is a microscopic image of microspheres prepared according to the disclosure, with 12% w/v PLA and 24% w/v ENG in the core solution, and 12% w/v PLA in the shell solution.
Figure 2C:
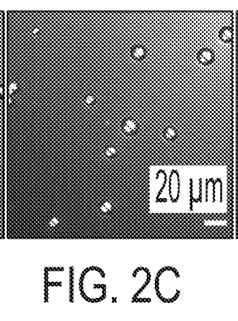
FIG. 2C is a microscopic image of microspheres prepared according to the disclosure, with 15% w/v PLA and 30% w/v ENG in the core solution, and 15% w/v PLA in the shell solution.
Figure 2D:
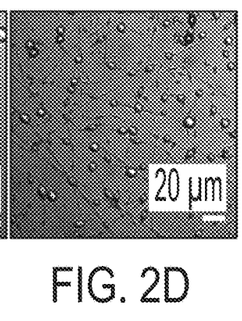
FIG. 2D is a microscopic image of microspheres prepared according to the disclosure, with 18% w/v PLA and 30% w/v ENG in the core solution and 18% w/v PLA in the shell solution.

The resulting microspheres for each of formulations 1-4 were evaluated under a confocal microscope. As shown in FIGS. 2A-2C (corresponding to Formulations 1-3, respectively), increasing the concentration of PLA in the formulation led to increased particle sizes. However, at 18% w/v PLA (Formulation 4, as shown in FIG. 2D), polymer fibers, rather than microspheres, began to form. Accordingly, it was determined that the concentration of the PLA in a microsphere can impact the formation of microspheres. In particular, for a theoretical drug loading of 50%, RESOMER® R 205 S should be present in an amount of less than about 18% w/v in order to avoid the formation of polymer fibers. Without intending to be bound by theory, it is believed that either or both of the amounts of PLA in the core or shell can affect the formation of microspheres, as compared to polymer fibers.

Based on the results obtained from evaluating the various formulations, it was determined that a 15% w/v PLA solution in the core and shell provided the best microspheres. Accordingly, microspheres having this concentration of PLA were prepared under different jetting conditions to evaluate the effect these conditions had on microsphere preparation.

TABLE 2

Jetting Conditions for Microsphere Formation

| | Core | | Shell | Theoretical | Jetting Conditions | | |
| | | | | | Core pump | Shell pump | |
| Formulation | PLA (% w/v) | ENG (% w/v) | PLA (% w/v) | Drug Loading | speed (mL/hr) | speed (ml/hr) | Voltage |
|---|---|---|---|---|---|---|---|
| 5 | 15 | 30 | 15 | 50 | 0.4 | 0.4 | 7→12 |
| 6 | | | | | 0.5 | 0.5 | 7→12 |
| 7 | | | | | 0.6 | 0.6 | 7→12 |

Figure 3A:
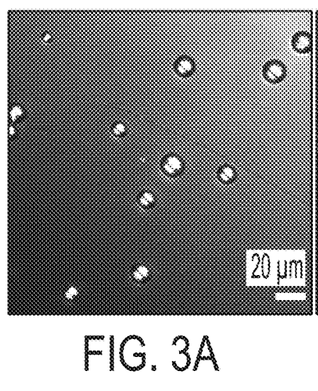
FIG. 3A is a microscopic image of microspheres prepared according to the disclosure, using a core and shell pump speed of 0.4 mL/hr.
Figure 3B:
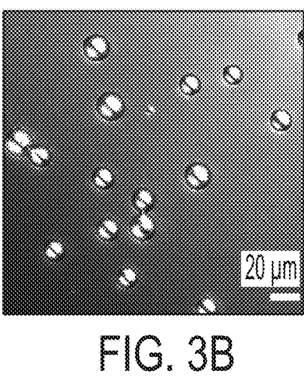
FIG. 3B is a microscopic image of microspheres prepared according to the disclosure, using a core and shell pump speed of 0.5 mL/hr.
Figure 3C:
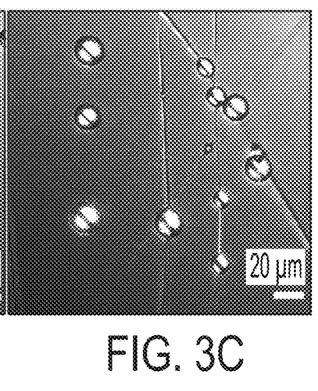
FIG. 3C is a microscopic image of microspheres prepared according to the disclosure, using a core and shell pump speed of 0.6 mL/hr.

The resulting microspheres for each set of jetting conditions (i.e., formulations 5-7) were evaluated under a confocal microscope. As can be seen by comparing FIG. 3A (corresponding to formulation 5) and FIG. 3B (corresponding to formulation 6), increased jet pump speeds resulted in microspheres having a larger particle size. However, as shown in FIG. 3C (corresponding to formulation 7), at 0.6 mL/hr pump speeds, polymer fibers were formed.

Figure 4A:
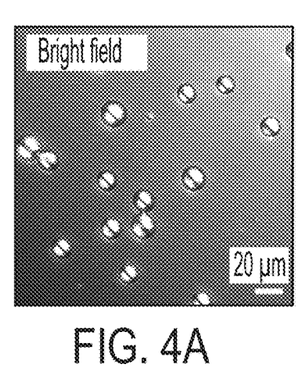
FIG. 4A is a bright field microscopic image of microspheres prepared according to the disclosure.
Figure 4B:
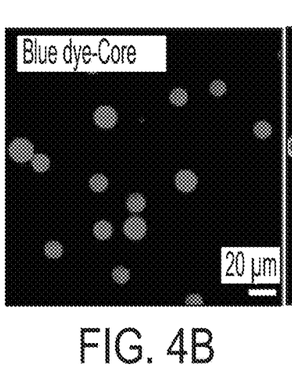
FIG. 4B is a microscopic image of microspheres prepared according to the disclosure where the core has been labeled with a blue fluorescent dye.
Figure 4C:
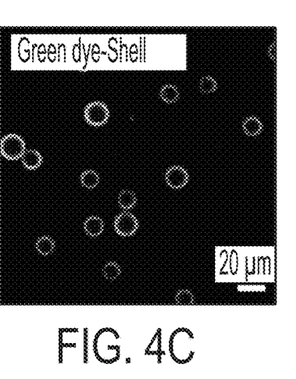
FIG. 4C is a microscopic image of microspheres prepared according to the disclosure where the shell has been labeled with a green fluorescent dye.

Furthermore, to confirm the core-shell structure, the core and shell were fluorescently labeled with blue and green dyes, respectively, and examined under a confocal microscope. As shown in FIGS. 4A-4C, the microspheres had a clear core-shell structure, indicating that the jetting method of preparing the microspheres was efficient in achieving the desired arrangement. The resulting microspheres had a particle size of approximately 12-18 μm, with a shell thickness of approximately 2-3 μm.

Therefore, Example 1 demonstrates that increasing polymer concentrations in the core and shell solutions from 10% w/v to 15% w/v can significantly increase the particle size of the microspheres, while fibers were formed when the polymer was included of more than 18% w/v. At 15% PLA, faster jetting pump speed resulted in larger particles. Furthermore, Example 1 demonstrates that the microspheres displayed a more homogeneous size distribution at a flow rate of 0.5 mL/h, whereas further increasing pump speed produced polymer fibers. Thus, the pump speed(s) can impact the effective formation of the microspheres. Example 1 also demonstrates that a stable Taylor-Cone was formed in the voltage range of 7-12 kV.

Example 2—Evaluation of the Collection Method of Microspheres

Microspheres were collected by each of Method 1 and Method 2, as described above. Particle morphology of the microspheres, collected according to each method, was evaluated via SEM to determine the effect of the collection method on microsphere morphology and size.

Figure 5A:
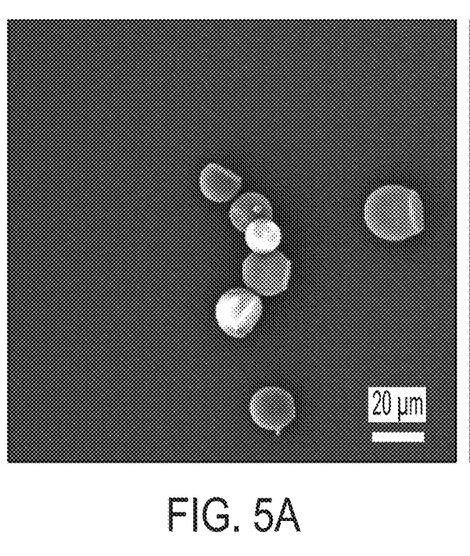
FIG. 5A is a scanning electron microscope (SEM) image of microspheres collected on an aluminum foil.
Figure 5B:
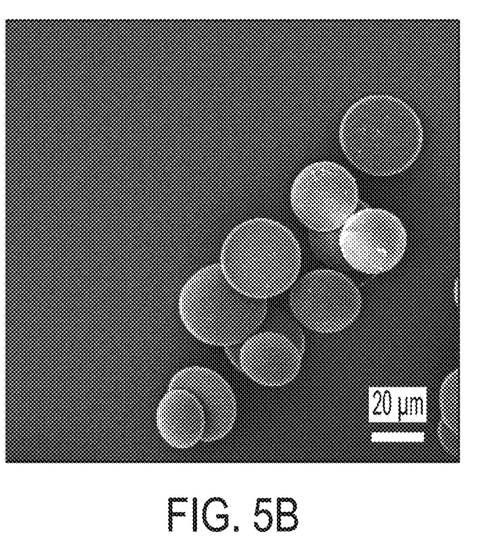
FIG. 5B is a scanning electron microscope (SEM) image of microspheres collected in a water bath with 1% PVA.

The resulting SEM images are shown in FIGS. 5A and 5B for Methods 1 and 2, respectively. As shown by comparing these images, the microspheres collected in the water bath have 1% PVA (i.e., Method 2) provided a more intact surface for the microspheres.

Thus, Example 2 demonstrates that the method of collection of the microspheres prepared by the EHD co-jetting method described herein can impact the surface and particle morphology of the resulting microspheres.

Example 3—In Vitro Release Studies of Microspheres

Microspheres having various compositions of the core and shell were prepared and tested for in vitro drug release. The compositions of the core and shell are provided in Table 3, below.

TABLE 3

Microsphere Formulations for In Vitro Release Studies

|   | Composition in different formulations (mg) | | | | Pump jetting speed (mL/hr) | | Theoretical Drug Loading (%) | Measured Drug Loading (%) |
|---|---|---|---|---|---|---|---|---|
|   | CORE | | SHELL | | | | | |
|   | PLA | ENG | PLA | ENG | CORE | SHELL | | |
| A | 150 | 300 | 150 | 0 | 0.5 | 0.5 | 50 | 49 ± 3 |
| B | 150 | 150 | 150 | 150 | 0.5 | 0.5 | 50 | 50 ± 2 |
| C | 100 | 300 | 150 | 0 | 0.5 | 0.5 | 55 | 54 ± 2 |
| D | 100 | 300 | 150 | 0 | 0.5 | 0.35 | 59 | 58 ± 2 |
| E | 100 | 300 | 100 | 0 | 0.5 | 0.5 | 60 | 58 ± 4 |
| F | 80 | 320 | 150 | 0 | 0.5 | 0.5 | 58 | 55 ± 4 |
| G[†] | 75 | 150 | 75 | 0 | 0.5 | 0.5 | 50 | 50 ± 2 |
| H | 100 | 300 | 150 | 0 | 0.5 | 0.5 | 55 | 54 ± 4 |

[†]15% w/v Resomer® R 207S PLA has very high viscosity (1.3-1.7 dL/g) which was expected to generate fibers instead of microspheres, thereby PLA % decreased in 7.5% w/v in formulation G.

As can be seen from Table 3, the drug loading efficiency was >95% for all formulations, indicating that the EHD co-jetting method effectively provided microspheres containing nearly all of the drug that was added to the core composition.

Figure 6A:
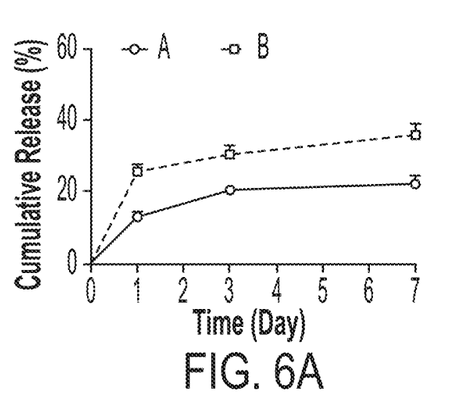
FIG. 6A is a graph of the cumulative release of a therapeutic agent from microspheres prepared according to the disclosure.

The release of the drug in from the microspheres in a PBST release medium was evaluated. FIG. 6A demonstrates the effect of the drug distribution within the microsphere on drug release. As shown in FIG. 6A, Formulation B, which contained 15% w/v ENG in the shell, as well 15% w/v ENG in the core, demonstrated a higher initial release of drug as compared to Formulation A, which contained the same amount of ENG (i.e., 30% w/v), but within the core only. After the initial burst of release seen at about 1 day, both formulations released ENG at relatively the same rate. Without intending to be bound by theory, it is believed that the initial quick release rate of Formulation B was due to the ENG releasing from the shell (e.g., drug could have migrated into the shell during manufacture), after which the rate slowed and was consistent with that of Formulation A, which was indicative of the drug being released from the core. Alternatively, or additionally, the ENG may have been subject to degradation, which could have caused a steady decrease in drug release with time.

Figure 6B:
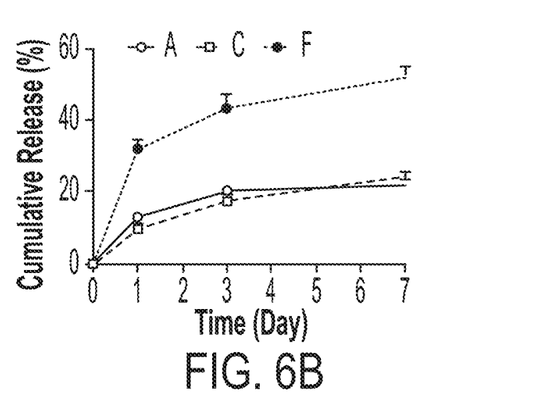
FIG. 6B is a graph of the cumulative release of a therapeutic agent from microspheres prepared according to the disclosure.

FIG. 6B demonstrates the effect of the polymer/drug ratio in the core on drug release. Formulation F, having a PLA: ENG ratio of 1:4 demonstrated significantly increased rates and overall release of ENG from the microsphere. However, each of Formulation A, having a PLA:ENG ratio of 1:2, and Formulation C, having a PLA:ENG ratio of 1:3 demonstrated very similar rates and overall release percentages.

Figure 6C:
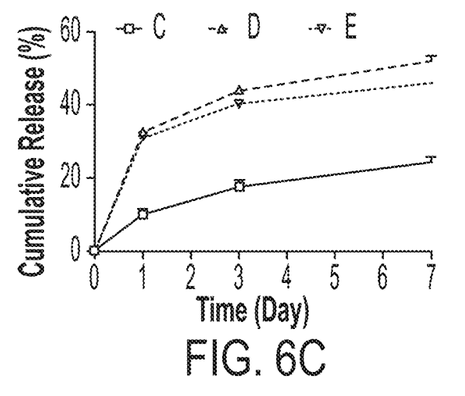
FIG. 6C is a graph of the cumulative release of a therapeutic agent from microspheres prepared according to the disclosure.

FIG. 6C demonstrates the effect of the shell thickness on drug release. Formulation C, having 15% w/v PLA in the shell and prepared with a shell pump jetting speed of 0.5 mL/hr had the slowest, most controlled release. Formulation D, also having 15% w/v PLA in the shell, but prepared with a shell pump jetting speed of 0.35 mL/hr, resulted in much higher rates of release than Formulation C. These results suggest that a slower shell pump jetting speed can result in a thinner shell in the microsphere. Furthermore, Formulation E, having 10% w/v PLA in the shell but shell a pump jetting speed of 0.5 mL/hr (i.e., the same as for Formulation C), performed very similarly to Formulation D. Accordingly, these results demonstrate that a thinner shell, which can be achieved by reducing the amount of polymer in the shell and/or by decreasing the shell pump jetting speed, can promote quicker release of the drug from the microsphere, while a thicker shell can provide a more stable and constant release profile.

Figure 6D:
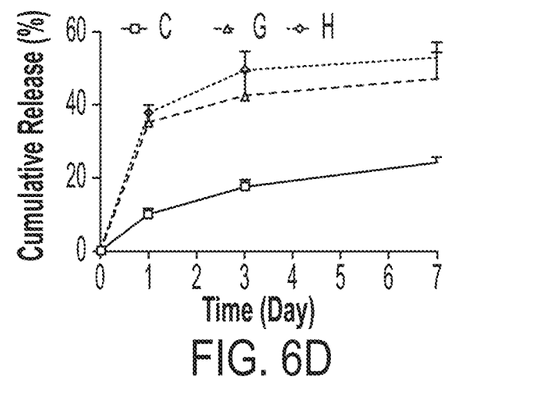
FIG. 6D is a graph of the cumulative release of a therapeutic agent from microspheres prepared according to the disclosure.

FIG. 6D demonstrates the effect of polymer type on drug release. As shown in FIG. 6D, Formulation H, having a low inherent viscosity (0.25-0.35 dL/g) PLA in both the core and the shell resulted in a high initial rate of release and the highest total release of the drug over 7 days. Formulation G, having a high inherent viscosity (1.3-1.7 dL/g) PLA in both the core and the shell, had a similar initial rate of release as Formulation H, but a steadier release after the first day. Each of Formulation G and H demonstrated a release profile with a high initial burst of the drug from the microspheres. In contrast, Formulation C, having a medium viscosity (0.55-0.75 dL/g) had the steadiest release rate, and the lowest overall release of the drug over 7 days. It was generally expected that of Formulations H, G and C, Formulation H would have the quickest release profile, due to the low viscosity of the PLA. Furthermore, Formulation G, even though it included a PLA with a high inherent viscosity, had the lowest concentration of PLA (in order to prevent the formation of polymer fibers upon manufacture) which was believed to contribute to the formation of more pores in the shell. Accordingly, the release profile of Formulation G was similar to that of H.

Figure 6E:
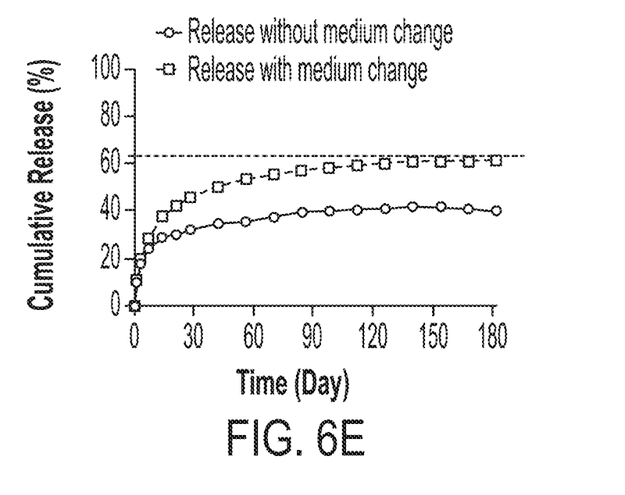
FIG. 6E is a graph of the cumulative release of a therapeutic agent from microspheres prepared according to the disclosure, with and without a change in medium.

FIG. 6E demonstrates the effect of medium changes on drug release of Formulation C over an extended term. Results indicated that drug release from the microspheres continued for at least 180 days.

Figure 7A:
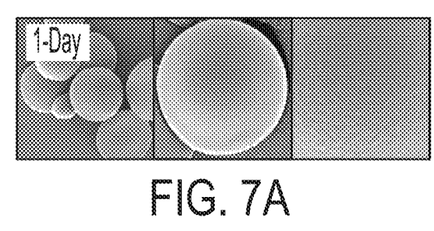
FIG. 7A is an SEM image of microspheres prepared according to the disclosure after 1 day of in vitro release.
Figure 7B:
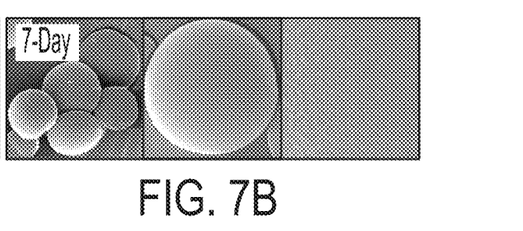
FIG. 7B is an SEM image of microspheres prepared according to the disclosure after 7 days of in vitro release.
Figure 7C:
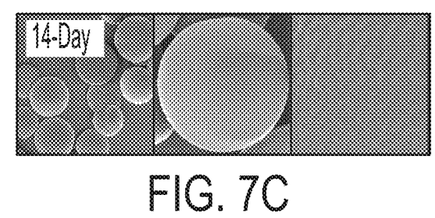
FIG. 7C is an SEM image of microspheres prepared according to the disclosure after 14 days of in vitro release.
Figure 7D:
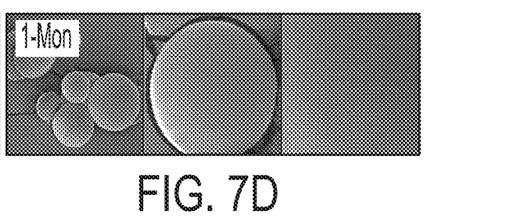
FIG. 7D is an SEM image of microspheres prepared according to the disclosure after 1 month of in vitro release.
Figure 7E:
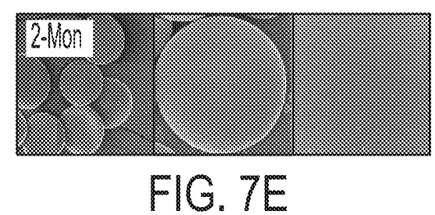
FIG. 7E is an SEM image of microspheres prepared according to the disclosure after 2 months of in vitro release.
Figure 7F:
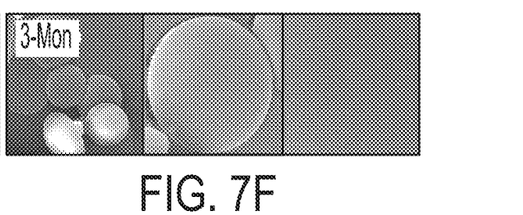
FIG. 7F is an SEM image of microspheres prepared according to the disclosure after 3 months of in vitro release.
Figure 7G:
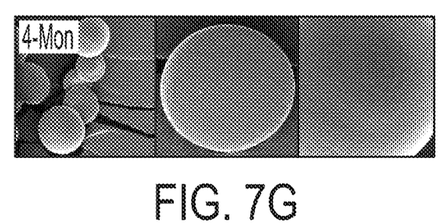
FIG. 7G is an SEM image of microspheres prepared according to the disclosure after 4 months of in vitro release.
Figure 7H:
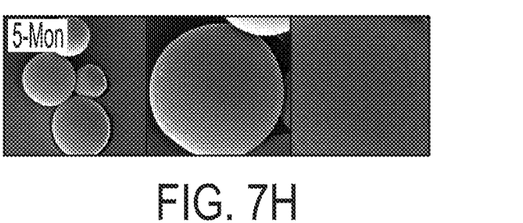
FIG. 7H is an SEM image of microspheres prepared according to the disclosure after 5 months of in vitro release.
Figure 7I:
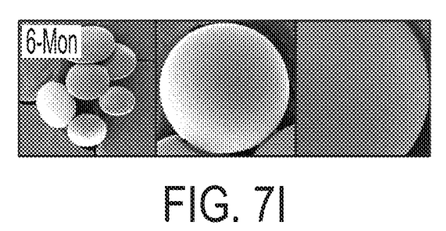
FIG. 7I is an SEM image of microspheres prepared according to the disclosure after 6 months of in vitro release.

The surface morphology of the microspheres after in vitro release were observed after various times points (i.e., 1 day, 7 days, 14 days, 1 month, 2 months, and 3 months). As can be seen by comparing the images in FIGS. 7A and 7F, the surface morphology of the microspheres after in vitro release for 3 months was still smooth, spherical, and integrate.

Accordingly, Example 3 demonstrates that the selection and amounts of the polymer and the drug, as well as the pump speeds of the shell can influence the release profile of the drug from the microspheres according to the disclosure. Furthermore, periodic changing of the microsphere release medium can help lengthen the duration of release of drug from the microspheres over time. Example 3 also demonstrates that drug loading of the microspheres can be achieved at levels of at least about 50% to about 60% with an encapsulation efficiency >95%.

Example 4—In Vivo Microsphere Evaluation

The microspheres of Formulation C were further evaluated in vivo by administering the microspheres to SD female rats. Two dosage levels were tested: about 6 mg/rat (high dosage group) and about 1 mg/rat (low dosage group). The pharmacokinetic (PK) evaluation data of the drug concentration in the blood are shown in FIG. 8.

Figure 8:
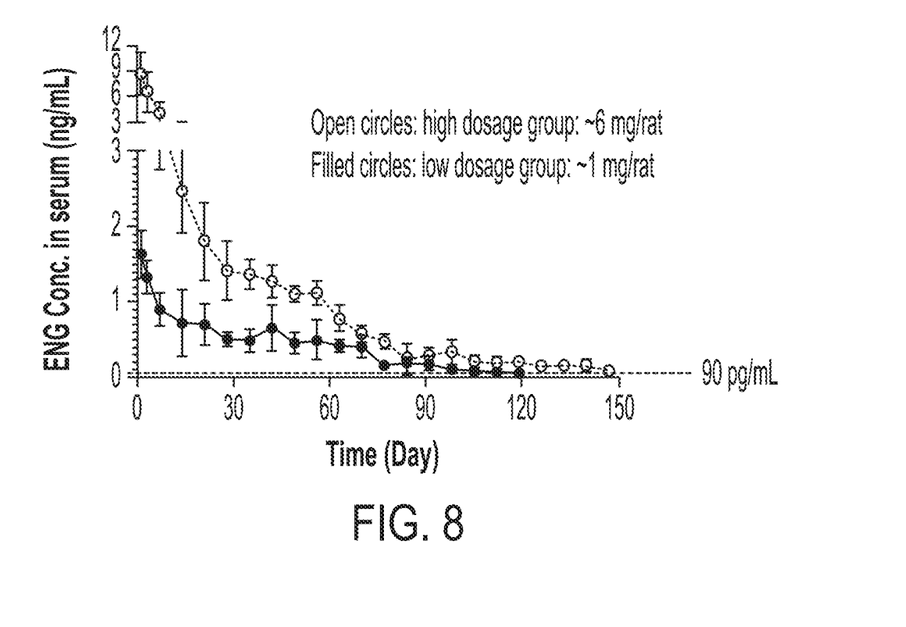
FIG. 8 is a graph of in vivo therapeutic agent concentration in serum after administration of the microspheres according to the disclosure.
Figure 9:
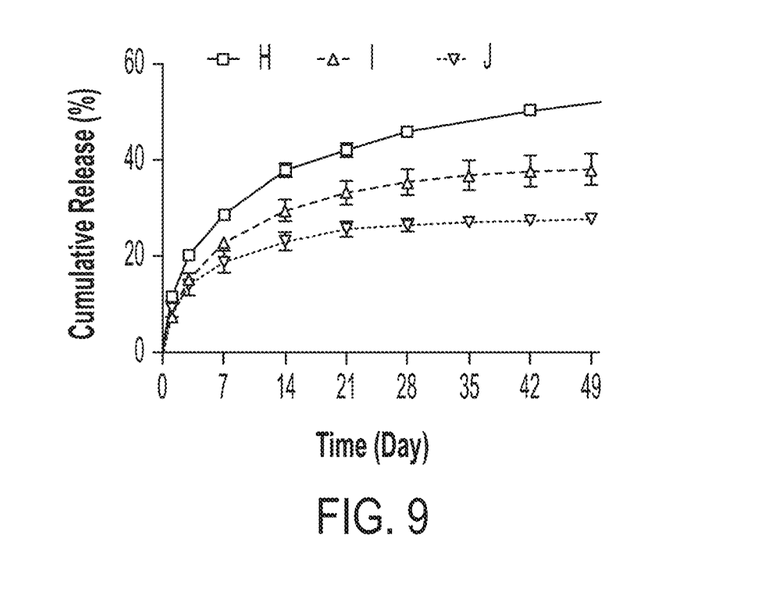
FIG. 9 is a graph of the cumulative release of a therapeutic agent from microspheres prepared according to the disclosure.
Figure 10A:
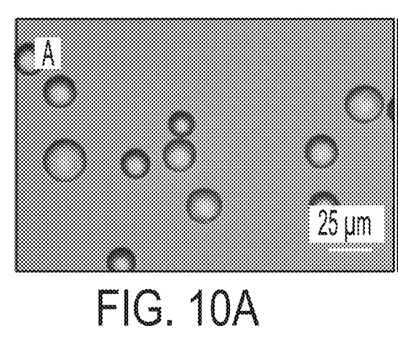
FIG. 10A is a microscopic image of microspheres prepared according to the disclosure, with a jetting needle working distance of 5 cm and a voltage of 7 kV.
Figure 10B:
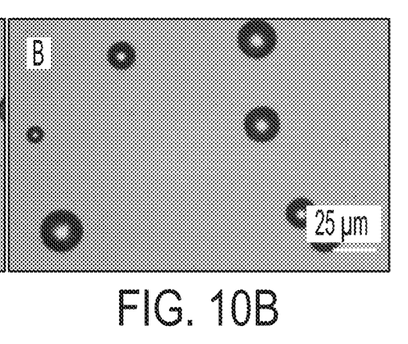
FIG. 10B is a microscopic image of microspheres prepared according to the disclosure, with a jetting needle working distance of 10 cm and a voltage of 7.5 kV.
Figure 10C:
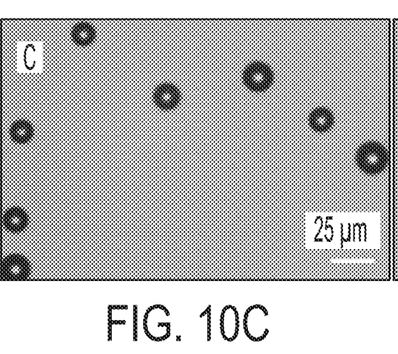
FIG. 10C is a microscopic image of microspheres prepared according to the disclosure, with a jetting needle working distance of 15 cm and a voltage of 8 kV.
Figure 10D:
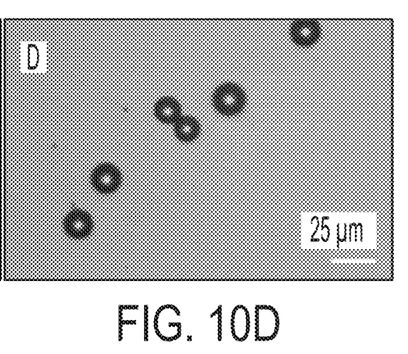
FIG. 10D is a microscopic image of microspheres prepared according to the disclosure, with a jetting needle working distance of 20 cm and a voltage of 8.5 kV.

As shown in FIG. 8, the in vivo ENG blood concentrations were maintained higher than 90 μg/mL for 98 and 147 days in the low and high dosage groups, respectively. Notably, 90 μg/mL is the effective blood concentration of ENG.

Accordingly, Example 4 demonstrates that the microspheres according to the disclosure are capable of providing a suitable release in vivo, maintaining an effective level in the blood, for at least about 5 months.

Example 5—Formulation Modifications and Initial Burst Release Analysis

Microspheres having various compositions of the core and shell were prepared, tested, and compared to evaluate the initial burst of in vitro drug release. The compositions of the core and shell, are provided in Table 4, below. The pump jetting speed of each of the core and shell was 0.5 mL/hr.

TABLE 4

Microsphere Formulations for In Vitro Initial Burst Release Studies

| | Composition in different formulations (mg) | | | | | Solvent, Volume (mL) | | Theoretical Drug Loading (%) | Measured Drug Loading (%) |
|---|---|---|---|---|---|---|---|---|---|
| | CORE | | SHELL | | | | | | |
| | PLA | ENG | PLA | ENG | Cholesterol | CORE | SHELL | | |
| H | 100 | 300 | 150 | 0 | 0 | CF, 1 | CF:EA†, 0.5:0.5 | 55 | 54 ± 4 |
| I | 100 | 300 | 150 | 0 | 0 | CF, 1 | DCM:EA†, 0.5:0.5 | 55 | 50 ± 2 |
| J | 100 | 300 | 150 | 0 | 30 | CF, 1 | DCM:EA†, 0.5:0.5 | 52 | 48 ± 2 |

†Boiling point of solvent: chloroform (CF): 61° C., ethyl acetate (EA): 77° C., methylene chloride (DCM): 39° C.

Compared to original Formulation H (shown again for convenience in Table 4), the shell solvent in Formulation I was changed from chloroform and ethyl acetate to methylene chloride and ethyl acetate at 1:1 ratio, which had lower boiling point than the cosolvent of chloroform and ethyl acetate. Without intending to be bound by theory, it was believed that the faster the shell dried, the less partition of drug from the core into the shell layer would occur. Moreover, cholesterol was incorporated into the shell composition of Formulation J to evaluate whether the incorporation of small molecules in the shell composition would help mitigate any saturation of drug in the shell and decrease the partition of drug from the core into the shell layer during formation of core-shell structure.

As shown in FIG. 10, the drug release from Formulation I was slower than that of Formulation H. FIG. 10 also shows that the burst release of Formulation J with about 5.17% w/v cholesterol in the shell (based on the total weight of the microsphere) was lower than that of each of Formulation H and Formulation I, which contained no cholesterol in the shell.

Accordingly, Example 5 demonstrates that each of decreasing the boiling point of the shell solvent (e.g., cosolvent) and incorporating small molecules within the shell composition can reduce the initial burst release of drug from the microsphere. Reduction of the initial burst release can advantageously result in a longer sustained release of the drug from the microsphere.

Example 6—Evaluation of Working Distance of Jetting Needle

The working distance between the jetting needle and the grounded collector was varied to evaluate the effect of the working distance on the dryness of the core-shell structured microspheres. The distance was evaluated with respect to Formulation I (see Table 4) as shown in Table 5, below. The pump jetting speed of each of the core and shell was 0.5 mL/hr.

TABLE 5

Effect of Working Distance on Core-Shell Structured Microsphere

| | Core | | Shell | Shell Solvent, | Jetting Conditions | |
|---|---|---|---|---|---|---|
| | PLA (% w/v) | ENG (% w/v) | PLA (% w/v) | Volume (mL) | Working distance (cm) | Voltage (kV) |
| I-1 | 10 | 30 | 15 | DCM:EA†, 0.5:0.5 | 5 | 7 |
| I-2 | | | | | 10 | 7.5 |
| I-3 | | | | | 15 | 8 |
| I-4 | | | | | 20 | 8.5 |

Microscopic images of the microspheres according to each of Formulation 1-1, 1-2, 1-3, and 1-4 were obtained, and are shown in FIGS. 11A, 11B, 11C, and 11D, respectively. As shown in these images, as the working distance and voltage between the jetting needle and grounded collector was increased, the particle size of the resulting microspheres decreased. Additionally, as the working distance and voltage increased, the apparent dryness of the shell or residual solvent remaining in appeared to decrease. As described in Example 5, increased shell dryness can reduce the initial burst release of drug from the microsphere.

Accordingly, Example 6 demonstrates that the working distance of the jetting needle to the grounded collector can impact the particle size of the microspheres and apparent dryness of the shell of the microspheres. By increasing the dryness of the microspheres, the particle size distribution of the micropsheres can be more homogeneous as a result of less swelling and shape change during collection of the microspheres.

The foregoing examples demonstrate the successful development of microspheres having a high-drug loading (54±2%), uniform particle size, and a clear core-shell structure with controlled shell thickness. Both in vitro release and in vivo PK studies strongly suggested that the microspheres are a very promising dosage form to achieve a sustained release of drug for three to six months.

What is claimed is:

1. A microsphere for extended, controlled release of a therapeutic agent, comprising:
a core comprising a first polymer and a poorly water-soluble therapeutic agent having a solubility in water of 50 µg/mL or less, the core comprising an interconnected porous network, wherein the core has a radius of about 4 µm to about 60 µm; and
a substantially impermeable shell surrounding the core, thereby limiting diffusion from the core, the shell comprising a second polymer, wherein the shell has a thickness of about 1 µm to about 20 µm;
wherein the first polymer and the second polymer can be the same or different, and each of the first polymer and the second polymer comprises poly (lactic acid) (PLA), poly (lactic-co-glycolic acid) (PLGA) having a high content of lactic acid, or a combination thereof.

2. The microsphere of claim 1, wherein the first polymer comprises PLA.

3. The microsphere of claim 1, wherein the first polymer comprises PLGA having a lactic acid content of at least about 60%, based on the total content of glycolic acid and lactic acid monomer units in the PLGA.

4. The microsphere of claim 1, wherein the first polymer is present in the core in an amount of about 10 wt % to about 65 wt %, based on the total weight of the core.

5. The microsphere of claim 1, wherein the poorly water-soluble therapeutic agent comprises a steroid.

6. The microsphere of claim 1, wherein the poorly water-soluble therapeutic agent is present in an amount of about 35 wt % to about 90 wt %, based on the total weight of the core.

7. The microsphere of claim 1, wherein the second polymer comprises PLA.

8. The microsphere of claim 1, wherein the second polymer is present in the shell in an amount of at least about 90 wt %, based on the total weight of the shell.

9. The microsphere of claim 1, wherein the shell has a thickness of about 2 µm to about 15 µm.

10. The microsphere of claim 1, wherein the shell further comprises a small molecule in an amount of about 0.1 wt % to about 30 wt %, based on the total weight of the shell, wherein the small molecule is selected from the group consisting of cholesterol, a lipophilic vitamin, a derivative of any of the foregoing, and any combination of the foregoing.

11. The microsphere of claim 1, wherein:
the first polymer is PLA;
the second polymer is PLA; and,
the poorly water-soluble therapeutic agent is etonogestrel.

12. An injectable contraceptive formulation comprising the microsphere of claim 1 and a pharmaceutically acceptable excipient.

13. The microsphere of claim 1, wherein the poorly water-soluble therapeutic agent has a solubility in water of 10 µg/mL or less.

14. The microsphere of claim 1, wherein the first polymer is present in the core in an amount between 10 wt. % and 65 wt. %, based on the total weight of the core, the poorly water-soluble therapeutic agent is present in an amount of about 35 wt % to about 90 wt %, based on the total weight of the core, and the second polymer is present in the shell in an amount of at least about 90 wt %, based on the total weight of the shell.

* * * * *